(12) United States Patent
Altmann et al.

(10) Patent No.: US 11,058,497 B2
(45) Date of Patent: Jul. 13, 2021

(54) USE OF AUGMENTED REALITY TO ASSIST NAVIGATION DURING MEDICAL PROCEDURES

(71) Applicants: Biosense Webster (Israel) Ltd., Yokneam (IL); Acclarent, Inc., Irvine, CA (US)

(72) Inventors: Andres Claudio Altmann, Haifa (IL); Assaf Govari, Haifa (IL); Vadim Gliner, Haifa (IL); Itzhak Fang, Irvine, CA (US); Noam Rachli, Hadera (IL); Yoav Pinsky, Beit Keshet (IL); Itamar Bustan, Zichron Ya'akov (IL); Jetmir Palushi, Irvine, CA (US); Zvi Dekel, Zichron Ya'akov (IL)

(73) Assignees: Biosense Webster (Israel) Ltd., Yokneam (IL); Acclarent, Inc., Irvine, CA (US)

(*) Notice: Subject to any disclaimer, the term of this patent is extended or adjusted under 35 U.S.C. 154(b) by 0 days.

(21) Appl. No.: 16/229,629

(22) Filed: Dec. 21, 2018

(65) Prior Publication Data

US 2019/0192232 A1 Jun. 27, 2019

Related U.S. Application Data

(60) Provisional application No. 62/610,449, filed on Dec. 26, 2017.

(51) Int. Cl.
*A61B 34/20* (2016.01)
*A61B 17/24* (2006.01)
(Continued)

(52) U.S. Cl.
CPC ............ *A61B 34/20* (2016.02); *A61B 1/0005* (2013.01); *A61B 1/00009* (2013.01); *A61B 1/04* (2013.01);
(Continued)

(58) Field of Classification Search
CPC ......... A61B 34/20; A61B 34/25; A61B 90/36; A61B 1/00009; A61B 90/361;
(Continued)

(56) References Cited

U.S. PATENT DOCUMENTS

| 5,391,199 | A | 2/1995 | Ben-Haim |
| 6,239,724 | B1 | 5/2001 | Doron et al. |

(Continued)

FOREIGN PATENT DOCUMENTS

| WO | 96/05768 A1 | 2/1996 |
| WO | 2007/106046 A2 | 9/2007 |

(Continued)

OTHER PUBLICATIONS

Citardi, Augmented Reality for Endoscopic Sinus Surgery With Surgical Navigation: A Cadaver Study, Int Forum Allergy Rhinol. May 2016 ; 6(5): 523-528 (Year: 2016).*

(Continued)

*Primary Examiner* — Phuc N Doan
(74) *Attorney, Agent, or Firm* — Volpe Koenig

(57) ABSTRACT

Physicians performing invasive procedures require accuracy and precision when working with surgical tools. Surgical procedures are increasingly becoming minimally invasive, with physicians operating using cameras to view the surgery site and directing their tools through oculars or video displays. Ideally, the physician should be able to perform the invasive procedure while simultaneously observing both the real-time image of the patient and additional data critical for his medical decisions about the manipulation of the surgical tool and the next surgical step. The augmented reality navigation system of the present disclosure provides tool location visibility for invasive procedures through the use of location sensors included on a camera and/or on the tools used during a procedure. A location tracking system deter- (Continued)

mines and monitors the locations of the tools and camera based on the characteristics of signals detected by the sensors and displays informational overlays on images obtained with a camera.

17 Claims, 7 Drawing Sheets

(51) Int. Cl.
| | |
|---|---|
| A61B 90/00 | (2016.01) |
| A61B 1/00 | (2006.01) |
| G06T 7/73 | (2017.01) |
| A61B 34/00 | (2016.01) |
| A61B 5/00 | (2006.01) |
| G06T 11/00 | (2006.01) |
| A61B 5/06 | (2006.01) |
| G06F 3/01 | (2006.01) |
| A61B 1/04 | (2006.01) |
| A61B 1/233 | (2006.01) |

(52) U.S. Cl.
CPC ........... *A61B 1/233* (2013.01); *A61B 5/0077* (2013.01); *A61B 5/064* (2013.01); *A61B 5/066* (2013.01); *A61B 5/068* (2013.01); *A61B 5/743* (2013.01); *A61B 17/24* (2013.01); *A61B 34/25* (2016.02); *A61B 90/36* (2016.02); *A61B 90/361* (2016.02); *G06F 3/011* (2013.01); *G06T 7/74* (2017.01); *G06T 11/00* (2013.01); *A61B 2034/2051* (2016.02); *A61B 2034/2057* (2016.02); *A61B 2034/2065* (2016.02); *A61B 2034/2068* (2016.02); *A61B 2034/2072* (2016.02); *A61B 2034/254* (2016.02); *A61B 2034/256* (2016.02); *A61B 2090/365* (2016.02); *A61B 2090/373* (2016.02); *A61B 2090/3983* (2016.02); *A61B 2505/05* (2013.01); *G06T 2207/30204* (2013.01)

(58) Field of Classification Search
CPC ......... A61B 1/0005; A61B 1/04; A61B 1/233; A61B 5/0077; A61B 5/064; A61B 5/066; A61B 5/068; A61B 5/743; A61B 17/24; A61B 2034/2051; A61B 2034/2057; A61B 2034/2065; A61B 2034/2068; A61B 2034/2072; A61B 2034/254; A61B 2034/256; A61B 2090/365; A61B 2090/373; A61B 2090/3983; A61B 2505/05; G06T 7/74; G06T 11/00; G06T 2207/30204; G06F 3/011
See application file for complete search history.

(56) References Cited

U.S. PATENT DOCUMENTS

| | | | |
|---|---|---|---|
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 10,109,092 | B1* | 10/2018 | Hitchings, Jr. ......... G06T 11/60 |
| 2002/0065455 | A1 | 5/2002 | Ben-Haim et al. |
| 2002/0082498 | A1 | 6/2002 | Wendt et al. |
| 2003/0120150 | A1 | 6/2003 | Govari |
| 2003/0179308 | A1 | 9/2003 | Zamorano et al. |
| 2004/0068178 | A1 | 4/2004 | Govari |
| 2005/0203380 | A1 | 9/2005 | Sauer et al. |
| 2005/0215879 | A1 | 9/2005 | Chuanggui |
| 2006/0281971 | A1 | 12/2006 | Sauer et al. |
| 2008/0107241 | A1* | 5/2008 | Yatsenko ................. A61B 5/06 378/207 |
| 2011/0306986 | A1* | 12/2011 | Lee ........................ B25J 9/1689 606/130 |
| 2012/0108955 | A1* | 5/2012 | Razzaque ............ A61B 1/0005 600/424 |
| 2013/0129170 | A1* | 5/2013 | Zheng ..................... G06T 7/149 382/131 |
| 2014/0275760 | A1 | 9/2014 | Lee et al. |
| 2014/0303491 | A1* | 10/2014 | Shekhar ............... A61B 8/5261 600/424 |
| 2016/0078625 | A1* | 3/2016 | Tajbakhsh ............ G06K 9/4642 382/128 |
| 2016/0191887 | A1 | 6/2016 | Casas |
| 2016/0220105 | A1 | 8/2016 | Duret |
| 2017/0172662 | A1* | 6/2017 | Panescu ................. A61B 90/37 |
| 2017/0296292 | A1 | 10/2017 | Mahmood et al. |
| 2017/0366773 | A1* | 12/2017 | Kiraly .................... H04N 5/372 |
| 2018/0193097 | A1* | 7/2018 | Mclachlin .............. A61B 34/20 |
| 2018/0262743 | A1* | 9/2018 | Casas ................... H04N 13/296 |
| 2019/0015162 | A1* | 1/2019 | Abhari .................. A61B 34/20 |
| 2019/0175059 | A1* | 6/2019 | Godwin ................. A61B 34/20 |
| 2019/0254757 | A1* | 8/2019 | Piron ................... A61B 5/7405 |
| 2019/0340838 | A1* | 11/2019 | Gluhovsky ............ A61B 5/068 |

FOREIGN PATENT DOCUMENTS

| | | |
|---|---|---|
| WO | 2017/015738 A1 | 2/2017 |
| WO | 2017/066373 A1 | 4/2017 |

OTHER PUBLICATIONS

Mahmud, Computer vision and augmented reality in gastrointestinal endoscopy, Gastroenterology Report, 3(3), 2015, 179-184 (Year: 2015).*
Wang, Endoscope field of view measurement, Mar. 2017, Biomedical Optics Express, vol. 8, No. 3, pp. 1441-1454 (Year: 2017).*
Chen, Massive Colonoscopy Images Oriented Polyp Detection (Year: 2018).*
Extended European Search Report dated May 21, 2019 for European Patent Application No. 18215886.5.

* cited by examiner

USE OF AUGMENTED REALITY TO ASSIST NAVIGATION DURING MEDICAL PROCEDURES

BACKGROUND

Surgical procedures often suffer from issues of visibility of anatomy. Visual aids that assist with visualizing anatomical structures within the body exist. However, the effectiveness of such visual aids is limited due to the fact that anatomical structures are opaque and thus block visibility for other anatomical structures. The nature of a surgical procedure as involving insertion of one or more tools into a human body often leads to the inability to see exactly what is occurring with those tools. Improved techniques for obtaining visibility during procedures are constantly being developed.

SUMMARY

A method for providing an augmented reality display of a subject is provided. The method includes obtaining an image from a camera. The method also includes detecting a location of the camera. The method further includes identifying a field of view of the camera based on the location of the camera. The method also includes generating one or more overlay features corresponding to the field of view. The method further includes compositing the one or more overlay features with the image from the camera to form a composited image. The method also includes displaying the composited image on a display.

A system for providing an augmented reality display of a subject is provided. The system includes a workstation and a camera. The workstation is configured to obtain an image from the camera, detect a location of the camera, and identify a field of view of the camera based on the location of the camera. The workstation is also configured to generate one or more overlay features corresponding to the field of view. The workstation is further configured to composite the one or more overlay features with the image from the camera to form a composited image and display the composited image on a display.

A system for providing an augmented reality display of a subject is also provided. The system includes a workstation, a display, one or more tools, a camera, an endoscope, and an endoscope camera. The workstation is configured to obtain an image from the camera and detect a location of the camera. The workstation is also configured to identify a field of view of the camera based on the location of the camera. The workstation is further configured to generate one or more overlay features corresponding to the field of view of the camera, the one or more overlay features corresponding to the field of view of the camera being associated with anatomy of the subject or being associated with the one or more tools. The workstation is also configured to composite the one or more overlay features corresponding to the field of view of the camera with the image from the camera to form a composited image. The workstation is further configured to display the composited image on the display.

BRIEF DESCRIPTION OF THE DRAWINGS

A more detailed understanding can be had from the following description, given by way of example in conjunction with the accompanying drawings wherein.

DETAILED DESCRIPTION

Figure 1:
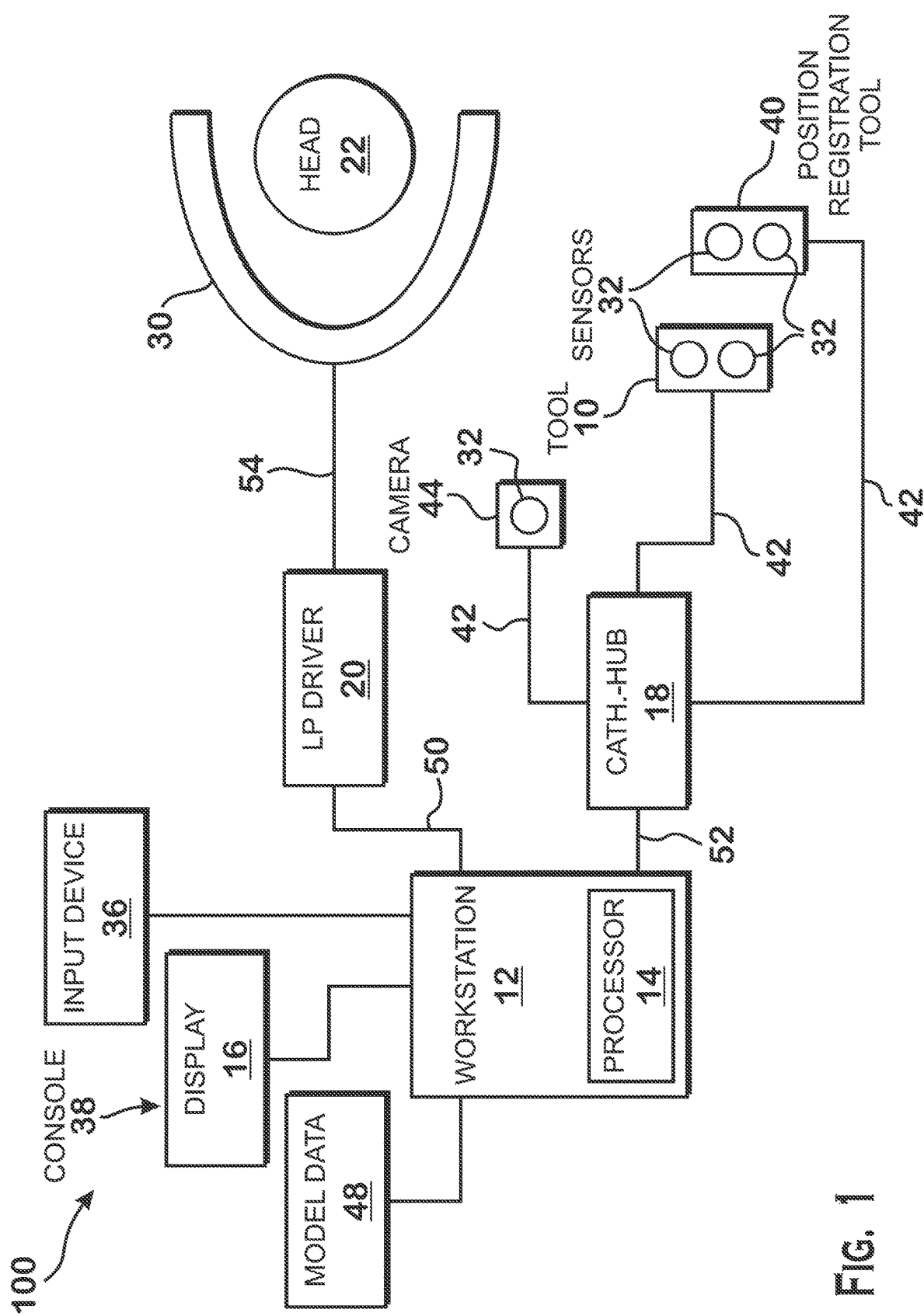
FIG. 1 is a schematic overview of a location tracking and navigation system in accordance with an embodiment of the present invention.

Physicians performing invasive procedures require accuracy and precision when working with surgical tools. Surgical procedures are increasingly becoming minimally invasive, with physicians operating using cameras to view the surgery site and directing their tools through oculars or video displays. Ideally, the physician should be able to perform the invasive procedure while, on a single display device, simultaneously observing both the real-time image of the patient and additional data critical for his medical decisions about the manipulation of the surgical tool and the next surgical step.

The augmented reality navigation system of the present disclosure provides tool location visibility for invasive procedures through the use of location sensors included on a camera and/or on the tools used during a procedure. A location tracking system determines and monitors the locations of the tools and camera based on the characteristics of signals detected by the sensors (such as amplitude or frequency of electromagnetic sensors). A registration process correlates a 3D model of the patient (generated, e.g., via a medical scan such as a computed tomography ("CT") scan) to the actual location of that patient. Thus the location of tools and the camera is tracked relative to the location of the anatomy of the patient. This relative location tracking allows for information related to the procedure to be composited with the image generated by the camera. For example, because the position of the camera relative to the tools is known, the location of the tools can be displayed within the image even when the tools are not visible to a human operator due to being occluded by tissue of the patient. This displaying is accomplished through standard three-dimensional ("3D") rendering techniques that render an image of an object relative to the position of a camera. More specifically, the position and orientation of the camera and tools are known relative to the position of a patient, through the function of the tracking system. Thus the position of tools is known relative to the field of view of the camera. Standard 3D rendering techniques display images of 3D objects based on the position of objects relative to a camera. Such techniques can be used to render images corresponding to the tools (e.g., a graphical representation of the tools) and additional compositing techniques can be used to display such rendered images over the image of the patient received from the camera. Additional information, such as a visualization of tools, rendering of anatomy, including display of three-dimensional structures of anatomy such as an artery or a network of blood vessels, a network of nerves, or the pre-operation identified borders of a tumor that is intended to be removed, or other information, could additionally or alternatively been shown in such a composited image.

One previous technology related to the present disclosure is the CARTO™ system, produced by Biosense Webster, Inc. (Diamond Bar, Calif.). Aspects of the CARTO™ system and of other related technologies can be found in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, which disclosures are all incorporated herein by reference.

FIG. 1 is a schematic overview of a location tracking and navigation system 100 in accordance with an embodiment of the present invention. As shown in FIG. 1, the system comprises one or more medical tools 10 (e.g., catheter, guidewire, endoscope, or the like), a camera 44 a console 38 comprising at least a work station 12 comprising at least a processor 14 and one or more display devices 16 (such as a monitor or a virtual reality display), a catheter hub 18, a location pad 30, a position registration tool 40, and a location pad driver ("LP driver") 20.

The workstation 12 is configured to communicate via a link 50 with the LP driver 20 to cause the LP driver 20 communicate via link 54 to drive field generators within the location pad 30. The field generators emit field signals (e.g., electromagnetic or other type of field such as acoustic) that is detected by the sensors 32. The sensors 32 generate response signals in response to the field signals. The response signals are sensed by the catheter hub 18. The catheter hub 18 communicates with sensors 32 on the tool(s) 10, camera 44, and position registration tool 40 via communication links 42. Communication links 42 may be wired or wireless links. The catheter hub 18 transmits to the response signals or processed versions of the response signals to the workstation 12 via link 52, which may be a wired or wireless link.

The workstation 12 determines position and physical orientation of the sensors 32, and thus of the objects the sensors 32 are incorporated within or attached to (e.g., the camera 44, the tool(s) 10, and the position registration tool 40) based on characteristics of the response signals. In one example, the field generators in the location pad 30 each have known relative locations. The sensors 32 receive signals from multiple field generators. The signals received can be differentiated based on time (e.g., different field generators are driven at different times so that the time at which the sensors 32 receive signals can be correlated to different field generators), frequency (e.g., different field generators are driven with signals of different frequencies so that the frequency of the signal received by the sensors 32 identifies individual field generators), or based on other characteristics of the signals generated by the field generators.

As described above, the catheter hub 18 transmits the signals (or processed versions of the signals) received from the sensors 32 to the workstation 12 for processing. The workstation 12 processes the signals to determine the location of the sensors 32 relative to the field generators of the location pad 30. The processing that is done to determine location of the sensors 32 depends on the type of signal emitted by the field generators. In some examples, the processing determines amplitude of the signals received in response to each of the field generators. A greater amplitude indicates a smaller distance to the field generator and a lower amplitude indicates a greater distance to the field generator. With distance determinations for multiple field generators per sensor 32 (e.g., 3), location relative to the field generators can be determined through triangulation. In an alternative, the field generators of the location pad 30 are instead sensors and the sensors on the tools are instead field generators. In such an alternative, the sensors of the location pad 30 detect signals emitted by the tools and the workstation 12 processes those signals in a similar manner as if the location pad 30 included the field generators and the tools included the sensors. Alternatively, any technically feasible technique for determining location based on response to signals can be used. Also, although a particular system for determining location of the tools is described, any technically feasible means for determining location of the tools may be used.

As described above, the system 100 also includes a position registration tool 40, which can be embodied as a handheld wand. The position registration tool 40 is used to correlate a three-dimensional model, stored in model data 48, with the locations of the field generators in the location pad in a registration procedure. In one example, the 3D model of the model data 48 is a computer data representation of the operation subject (e.g., the head 22 of a patient). This 3D model may be obtained through medical imaging techniques such as a computerized tomography ("CT") scan or magnetic resonance imaging ("MRI"), or any other imaging technique that produces data that can be converted into a 3D model. To perform the registration procedure, the position registration tool 40 is placed at a particular location in the vicinity of the subject (e.g., the head 22). The workstation 12 then associates that position with a position within the 3D model stored in the model data 48, thereby correlating a point in the 3D model to a point in reality. This association may be made in response to a specific indication by an operator such as a surgeon. In such a scenario, the workstation 12 displays the 3D model from the model data 48 on the display 16. The operator moves the position registration tool 40 to a particular location, and then indicates to the workstation 12 the corresponding location in the 3D model via the input device 36. In an alternative scenario, the workstation 12 automatically associates locations in real space with locations in the 3D model. In one example, this automatic association is done as follows. The position registration tool 40 is moved around the vicinity of the operation subject (e.g., the head 22). The workstation 12 processes data received from the position registration tool 40 to identify the corresponding location in the 3D model. In one example, the position registration tool 40 includes a camera and the workstation 12 performs image processing on images received with the position registration tool 40 to identify the location of the position registration tool 40 in the 3D model. In some examples, multiple points of correlation between real space and the 3D model are obtained and stored to improve the accuracy of the registration and to achieve rotational, as well as positional, registration. Although the position registration tool 40 is described as the tool being used to achieve registration of positions between real space and the 3D model, any other tool, including tools used for other purposes (such as the camera 44 or any of the tools 10) may alternatively be used.

The camera 44 provides a view in the display 16 for an operator. This view includes both an actual image of the subject (represented by head 22). More specifically, the camera 44 takes a series of images of the subject (head 22) and displays such images on the display 16.

In addition, the workstation 12 can overlay particular features on the images provided by the camera 44. More specifically, the camera 44 includes a location sensor 32 that, in conjunction with the location pad 30 (or alternatively in conjunction with some other mechanism), cooperates with the catheter hub 18 to provide a signal from which position and orientation of the camera 44 can be provided to the workstation 12. This position information can be derived in a similar manner as described above with respect to the cooperation of the location pad 30 and the sensors 32 on the tools 10 and position registration tool 40. Rotation of the camera 44 can be detected in any technically feasible manner. In one example, multiple different microsensors are included within the sensor 32 of the camera 44, and the relative measurements taken with the different microsensors are used to determine a rotation of the camera 44.

The workstation 12 uses the position and rotation information obtained for the camera 44 to provide one or more overlay features on the display 16, the overlay features being composited with the image generated by the camera. More specifically, based on the position and orientation of the camera 44, the workstation 12 is able to locate one or more virtual objects (e.g., anatomical labels) in the three dimensional space of the 3D model of the model data 48. Due to the linking between the 3D space of the 3D model with the coordinate system of reality (made via the position registration procedure), virtual objects (also referred to herein as "overlay features") linked to the 3D space of the 3D model can be displayed in the image taken with the camera.

Traditional 3D imaging techniques may be used to display some such overlay features in the image taken with the camera. In a simple example, the workstation 12 has the position of the camera 44 in real space and has correlated the geometry of a 3D model to real space via the registration procedure described above. Thus the workstation 12 knows the relative position of the 3D model and the camera 44 in the real space coordinate system. Traditional 3D rendering techniques, such as those implemented in standard commercially available 3D rendering graphics cards (such as the GeForce series of cards available from Nvidia corporation of Santa Clara Calif. or the Radeon series of cards available from Advanced Micro Devices, Inc., of Sunnyvale, Calif.), are able to draw three-dimensional objects to a screen space, given the positions of the objects in a coordinate system and given a camera position within that coordinate system. Such techniques could be used to render the 3D model of the model data 48 in the screen space displayed on the display 16. In some modes of operation, the workstation 12 renders the 3D model of the model data 48 and/or of other overlay features, discussed below, over the image provided by the camera 44. Thus, in such modes of operation, the workstation 12 produces an image including a 3D model-based overlay, composited with the camera 44-generated image. In some modes of operation, the workstation 12 displays no parts, some parts, or all parts of the 3D model, as well as no or some other overlay features. The overlay features include information related to a procedure performed on the subject (e.g., head 22), and/or related to the anatomy of the subject. Overlay features include user—(e.g., surgeon) generated tags for marking particular locations in the three-dimensional space of the subject. Overlay features alternatively or additionally include computer-generated features that are generated based on analysis of the image obtained via the camera 44. Overlay features could include any other data that is displayable on the display 16 that that indicates information related to a procedure performed on the subject or to any other aspect of usage of the system 100. In an example, the overlay features include markers pre-defined by a surgeon as a point of interest, as an identification of anatomy, as specifically-defined text, or as any other feature.

In another example, the overlay features include graphical representations of one or more tools 10. More specifically, the workstation 12 has the location of the sensors 32 on the tools relative to the camera 44. The workstation 12 can use similar techniques as discussed above to render a graphical representation of the tools in the image generated by the camera 44. The manner in which the graphical representations are rendered may depend on orientation (e.g., rotation) of the tools 10, in addition to the location of the tools 10, so that the physician understands the position of the geometry of the tools 10 relative to the anatomy of the patient.

The display 16 can be a traditional display or can be virtual reality glasses. The virtual reality glasses may have appropriate shielding, such as X-ray shielding provided by lead, if a procedure involves imaging appropriate for such shielding. The display 16 may also be a remote display (i.e., a display remotely located from the patient), which could facility remote surgery along with remotely controlled tools 10.

Additional details of the system 100 will now be described with respect to the remaining figures. These additional figures illustrate aspects of the system 100 in the context of an otorhinolaryngology procedure, although it should be understood that the general principles described could be used in other areas of the human body.

Figure 2:
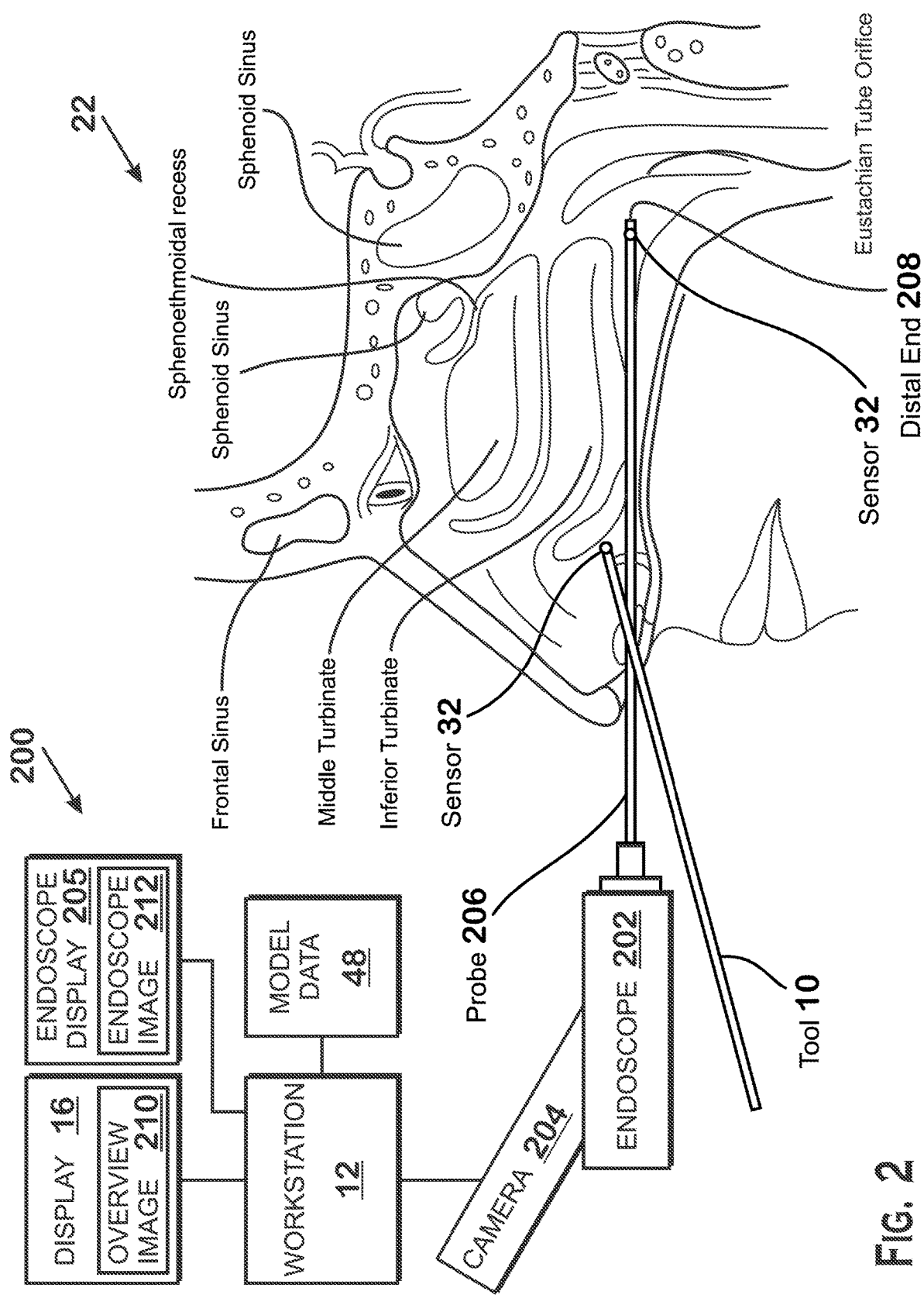
FIG. 2 illustrates parts of an example location tracking and navigation system including tools related to otorhinolaryngology.

FIG. 2 illustrates parts of an example location tracking and navigation system 200 including tools related to otorhinolaryngology. System 200 is an example of system 100 in which one of the tools 10 is an endoscope 202. The location tracking and navigation system 200 includes a display 16, which is similar to the display 16 of FIG. 1, and a workstation 12, similar to the workstation 12 of FIG. 1. The location tracking and navigation system 200 also includes other elements of the system 100 of FIG. 1, even if such elements are not illustrated in FIG. 2. Although the system 200 is described as including both the endoscope 202 and the camera 44, it is possible to use only an endoscope 202 without the camera 44.

One of the tools 10 of FIG. 2 is an endoscope 202, which includes a probe 206 that obtains an image at a distal end 208 and provides that image to a camera 204 connected to the endoscope 202. The camera 204 transmits the image to the workstation 12, which processes the image for display. The workstation 12 may display the image obtained with the camera 204 integrated with the endoscope 202 in the same display as the one that shows the image obtained with camera 44 illustrated in FIG. 1 (e.g., on display 16) or may show the image in a separate endoscope display 205. If shown on display 16, the workstation 12 performs operations so that the display 16 can be shared between the camera 204 and the camera 44. In one example, the display 16 is switched between showing an image from the camera 44 and the camera 204 in response to an input from the operator. For example, when the camera 204 is powered off, the display 16 may show the image from camera 44 and when the camera 204 is powered on, the display 16 may show the image from camera 204. Alternately, the selection of camera 44 or camera 204 may occur in response to an explicit camera selection input that explicitly selects which camera to show an image. If the endoscope display 205 is used to show the image from the camera 204 of the endoscope 202, then there is no contention between the displays—the display 16 shows the image from the camera 44 and the endoscope display 205 shows the image from the camera 204 of the endoscope 202. The image generated by camera 44 of FIG. 1 including the overlay features is the overview image 210 (shown on display 16).

As with the camera 44, the workstation 12 obtains the image from the camera 204, which is obtained by the endoscope 202, and displays that image on the display along with endoscope overlay features. The endoscope overlay features include information relevant to a procedure being performed and/or to the anatomy of the subject (e.g., head 22). Also, as with system 100, one or more tools 10 (e.g., surgical tools) may be present in the vicinity of the subject (e.g., head 22). FIG. 2 illustrates one tool 10 having a sensor 32. Also, at the end of the probe 206 of the endoscope 202 is a sensor 32. The workstation 12, in conjunction with the location pad 30, and location pad driver 20, detects the location and orientation of the sensors 32 and thus the location and orientation of the tools 10 and endoscope probe 206. It should be understood that FIG. 2 illustrates an example implementation and that any number of tools 10, each with sensors 32, could be used in a procedure. The image generated by the camera 204 and including the endoscope overlay features comprises the endoscope image 212, which again, may be displayed either on display 16 or on endoscope display 205.

The endoscope overlay features include indications of tool locations (such as tool 10 shown, or other tools), indications of anatomy locations or positions, or other indications related to the procedure or anatomy. In some modes of operation, the workstation 12 processes the location data generated based on the sensors 32 and uses that location data to generate overlay features for the endoscope image 212. Such overlay features include a visual image indicating position and orientation of the tool 10. As with the processing described with respect to FIG. 1, the workstation 12 uses the positions of the sensors 32, determined using the location pad 30, and the location and direction of the distal end 208 of the endoscope probe 206, also determined using the location pad 30, to determine locations and shapes of overlay features in the endoscope image 212. As described with respect to FIG. 1, standard three-dimensional rendering algorithms are able to generate an image given a camera position and orientation and an object position and orientation. The workstation 12, using such algorithms, is able to generate an image for the overlay feature corresponding to different tools based on the position of the tools 10 relative to the distal end 208 of the endoscope probe 206. The sensor 32 on the endoscope probe 206 is positioned at a known location relative to the distal end 208 of the endoscope probe 206 so that the location of the distal end 208 of the endoscope probe 206 can be derived from location data taken from the sensor 32 on the endoscope probe 206.

Figure 3:
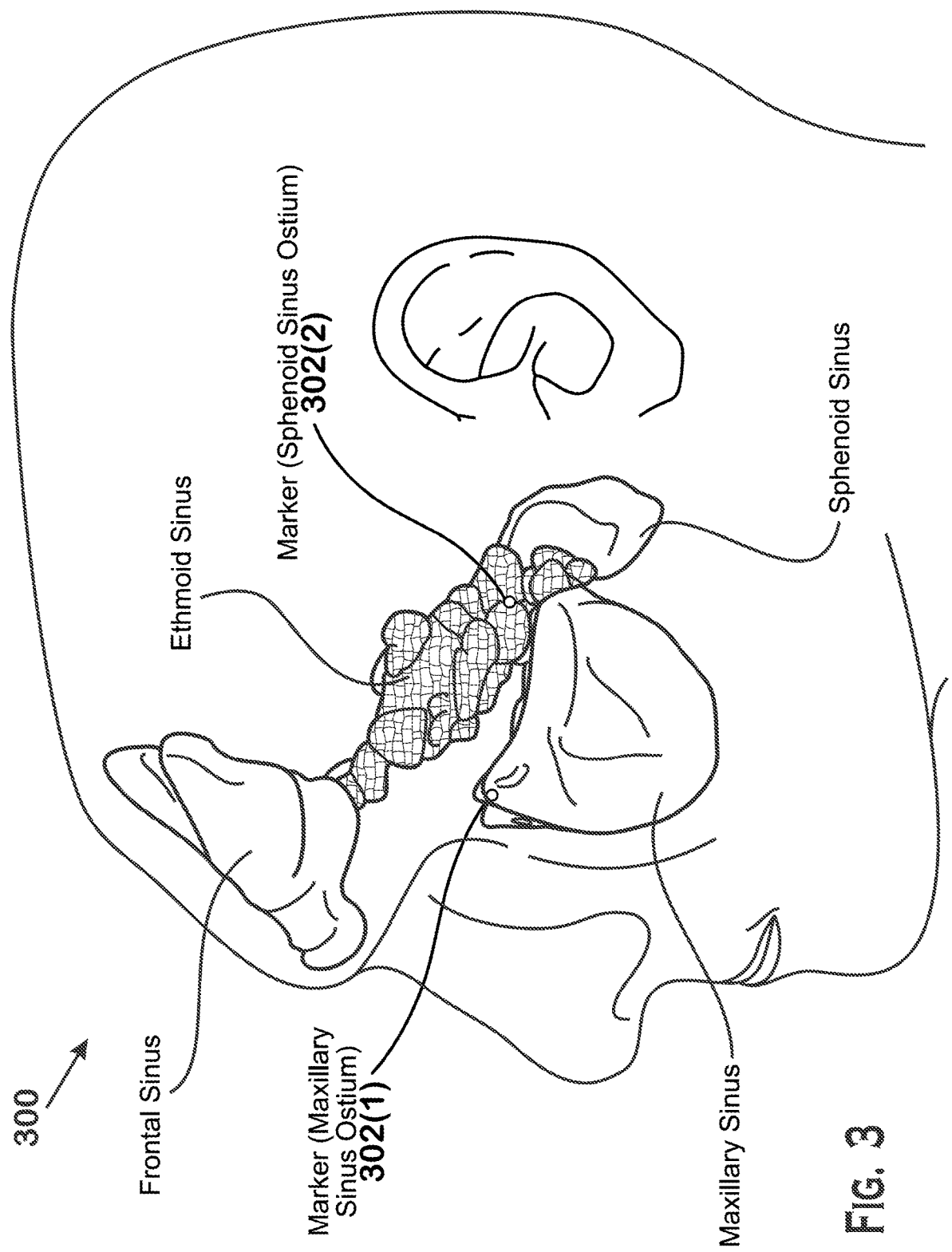
FIG. 3 illustrates a 3D model of a head, for the purposes of illustrating the context in which overlay features exist and/or for showing the manner in which at least some of the overlay features are generated, according to an example.

In addition to tool locations and orientation, in some modes of operation, the overlay features displayed by the workstation 12 in the endoscope image 212 also include text and graphical markers related to anatomy. FIG. 3 illustrates a 3D model 300 of a head, for the purposes of illustrating the context in which overlay features exist and/or for showing the manner in which at least some of the overlay features are generated, according to an example. The 3D model 300 may be obtained through standard medical imaging techniques such as a CT scan or a MRI and conversion of the data obtained through those techniques to a three-dimensional model using known techniques. Such a scan could occur prior to any procedure that uses the system 100 of FIG. 1 or the system of FIG. 2. For purposes of simplicity and clarity, only a few anatomical structures are shown in the 3D model 300. However, it should be understood that a 3D model used for a medical procedure and generated based on a scan could reflect substantially all anatomical structures of a subject.

In some modes of operation, at least some of the overlay features composited onto the endoscope image 212 are based on markers 302 input by a human operator. More specifically, prior to the procedure, a 3D model of the subject would be generated, for example, based on a medical scan. Subsequently, a human operator such as a surgeon would view the 3D model and would input markers 302 within the three-dimensional coordinate system of the 3D model. Any user interface could be used to allow the human operator to input the markers 302. Some examples of those markers 302 are illustrated in FIG. 3. Marker 302(1) is associated with the maxillary sinus ostium and marker 302(2) is associated with the sphenoid sinus ostium. Other markers 302 could be present in the 3D model as well.

Note that the computer system on which the markers 302 are input into the 3D model does not need to be the workstation 12. In other words, a 3D model may be analyzed and manipulated (have markers 302 added) by a human operator on a computer system that is different than the compute system (workstation 12) that generates the images (overview image 210, endoscope image 212) for viewing by the human operator during a procedure. For this reason, although it is sometimes stated herein that the workstation 12 performs certain tasks related to adding markers 302 to the 3D model 300 or performing other tasks related to adding, removing, editing, or otherwise manipulating data for overlay features, it should be understood that such actions could alternatively be performed with a different computer system.

In some modes of operation, the workstation 12 automatically generates markers. Some markers may be added based on an analysis of the 3D model 300 and based on well-known anatomy-related information. For example, the workstation 12 could generate a marker 302 for one or more particular anatomical structures based on a template 3D model that comprises a generic three-dimensional model of a human head and based on additional analysis such as a comparison of a 3D model of the human subject being operated on with the template model. In some examples, markers 302 are generated both automatically and with human input. More specifically, the workstation 12 automatically generates markers and a human adjusts the position of those markers. Alternatively, the workstation 12 presents a list of anatomical landmarks for which markers 302 can be automatically generated by the workstation 12. In response, the human operator selects one or more such landmarks and the workstation 12 generates markers 302 based on those selected landmarks. The human operator may subsequently adjust the position of those markers based on the actual structure of the subject's head. Any other technically feasible means for generating such markers 302 is possible as well. The markers 302 may include associated text, input by the human operator, as well. These text markers can be generated during input of the markers 302 themselves. For example, when the human operator selects a point in a 3D model as being a marker 302, the human operator may also input a text label.

Some overlay features, such as at least some of the markers 302, are displayed during a procedure in either or both of the overview image 210 or the endoscope image 212. As described above, since the workstation 12 knows where the camera 44 is, where the distal end 208 of the endoscope probe 206 is, and where the anatomy of the subject is, based on the registration procedure, the workstation 12 is able to render indicators for one or more of the sensors markers 302.

Figure 4B:
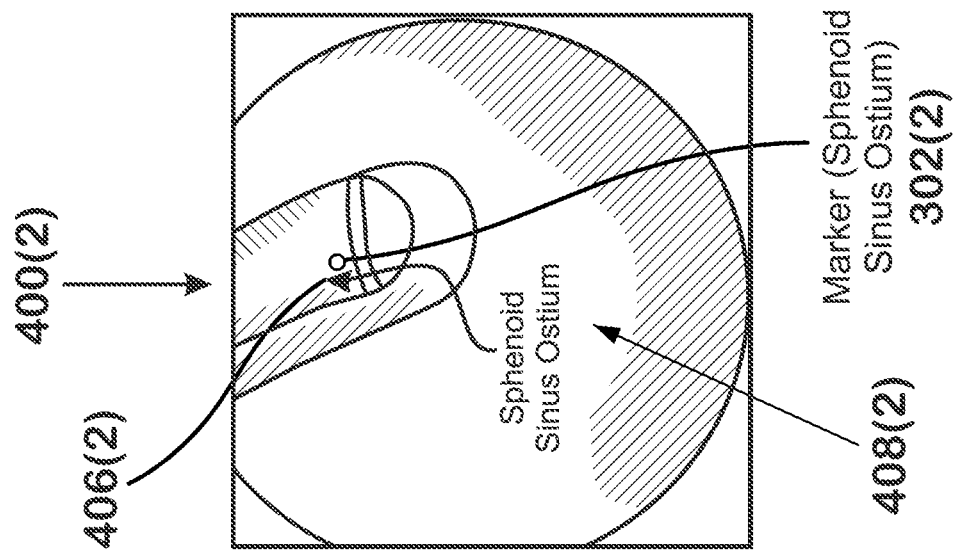
FIGS. 4A-4D illustrate example endoscope images.
Figure 4A:
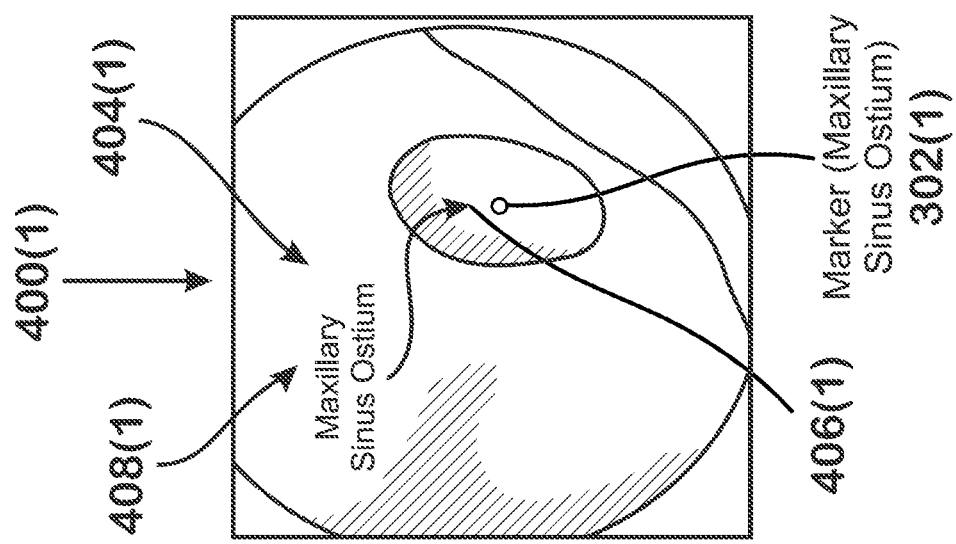
Figures 4C, 4D:
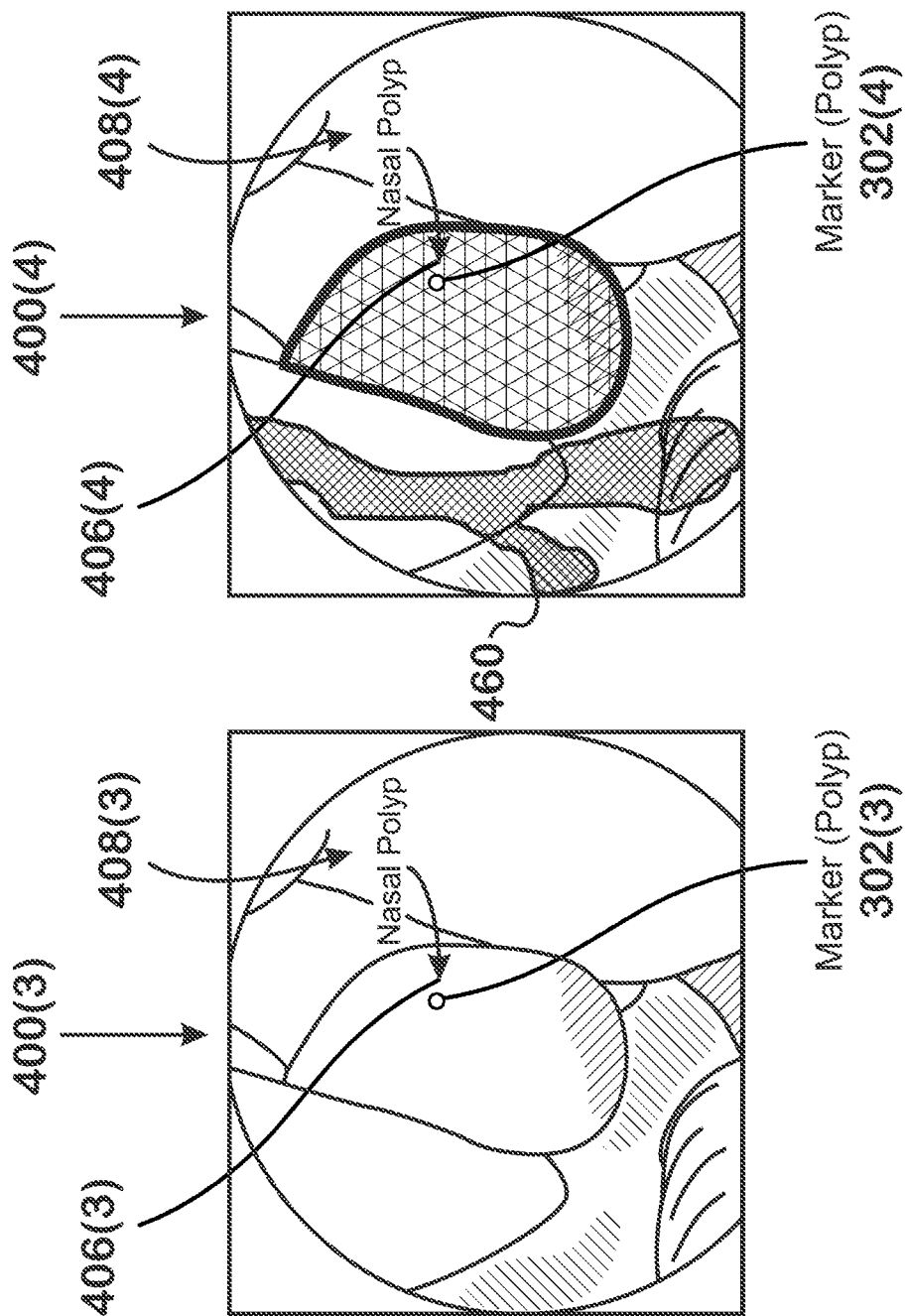

FIGS. 4A-4C illustrate example endoscope images 212. In image 400(1), the endoscope probe 206 is inserted into the nasal cavity pointed towards the maxillary sinus ostium, which is thus visible in the image 400(1). The 3D model includes a marker 302 at the maxillary sinus ostium. From analyzing the position of the marker 302 as compared with the position of the distal end 208 of the endoscope probe 206, the workstation 12 determines that the marker 302(1) is within the field of view of the endoscope camera 204. In response, the workstation 12 displays an overlay feature 404(1) associated with the marker 302 in the endoscope image 212. In image 400(1), the overlay feature includes an arrow 406(1) and text 408(1), however, the overlay could include other graphical features in other implementations. The graphical features of the overlay are configured to indicate the location of the marker 302. In the image 400(1), this indication is accomplished via the arrow 406 which extends from the approximate location of the marker 302 to text 408 associated with the marker 302. Other modes of operation could include different types of graphics configured to illustrate location of the marker 302 in different ways.

In the configuration in which the location of the marker 302 is indicated with an arrow 406 and text 408, the workstation 12 is configured to choose an appropriate location for the text 408 and then to draw an arrow 406 from the location corresponding to the marker 302 to the location chosen for the text 408. Any technically feasible means for analyzing an image to determine an appropriate location for text could be used. The term "appropriate" means generally that the text 408 is legible. In one example, a portion of the image 404 having a roughly even color is chosen for the text. In one example, roughly even color is determined based on the variance of the average color values for the pixels in an area. The higher the variance, the less even the area is. In an example, an area with variance below a particular threshold indicates that the area is appropriate for text. It should be noted that the techniques described above represent some examples of techniques for displaying an overlay and that any technically feasible means for displaying a feature identifying the location of a marker 302 could be used.

FIGS. 4B and 4C illustrate other example images 400 at other locations. Specifically, image 400(2) represents a view taken by the endoscope 202 with the endoscope probe 206 inserted into the nasal cavity and pointed towards the sphenoid sinus ostium. Based on marker 302(2), the workstation 12 generates the text 408(2) and the arrow 406(2) in a similar manner as described with respect to FIG. 4A. Image 400(3) represents a view taken by the endoscope 202 with the endoscope probe 206 inserted into the nasal cavity and pointed towards a nasal polyp. As with images 400(1) and 400(2), the workstation 12 generates image 400(3) based on position data from the sensors 32, based on the 3D model, and based on markers 302.

FIG. 4D illustrates another example image 400(4). Specifically, image 400(4) represents a view taken by the endoscope 202 with the endoscope probe 206 inserted into the nasal cavity and pointed towards a nasal polyp. Based on the marker 302(4), the workstation 12 generates the text 408(4) and the arrow 406(4). In addition, the workstation 12 has information indicative of the shape and location of a blood vessel 460. The workstation 12 determines that the blood vessel is within the field of view corresponding to the image taken by the endoscope 202 and thus displays a graphical representation of the blood vessel 460 in image 400(4). This allows a practitioner to avoid the blood vessel 460 during a procedure.

Figure 5B:
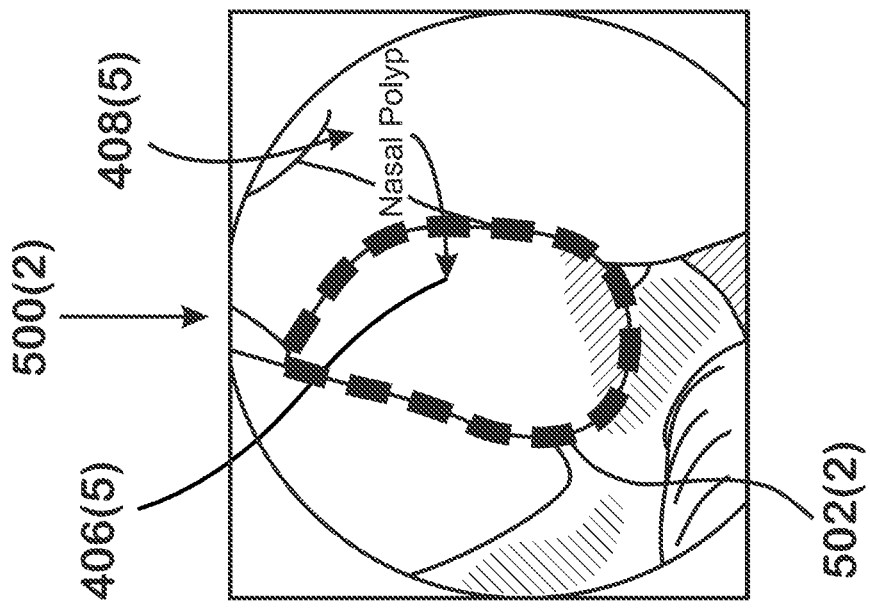
FIGS. 5A-5B illustrate examples images that include a type of overlay feature referred to as "anatomical feature outlines" herein.
Figure 5A:
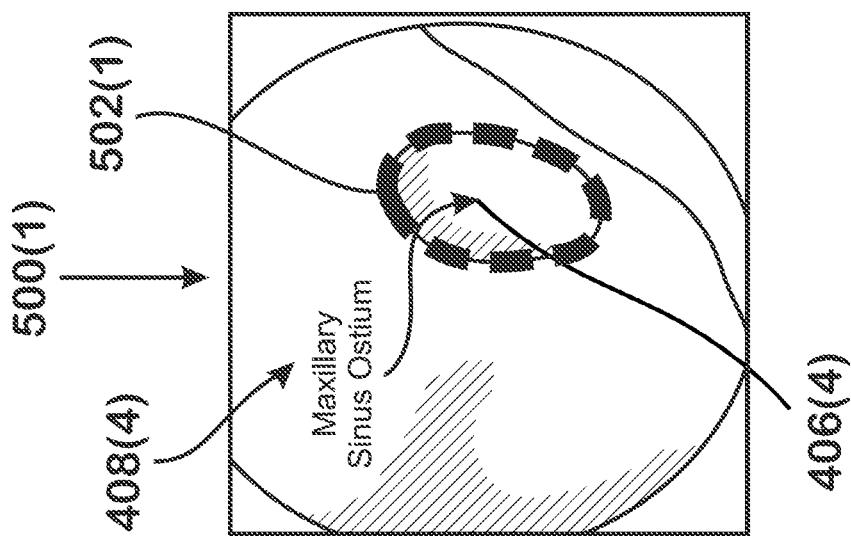

FIGS. 5A-5B illustrate examples images 500 that include a type of overlay feature referred to as "anatomical feature outlines" herein. These anatomical feature outlines 502 are automatically generated by the workstation 12 and are used to indicate the location of certain anatomical features. The image 500(1) illustrates an arrow 406(4) and text 408(4), as well as an outline 502(1). The outline 502(1) is automatically generated by the workstation 12 by image processing, potentially in combination with the positional information received from the sensors 32 and with the 3D model information stored in model data 48.

The workstation 12 could perform any technically feasible means for identifying the geometrical outline of particular anatomical features of interest. In one example, a template model of an "ideal" or "reference" anatomy is compared with the 3D model obtained from an actual scan of a subject. Known anatomical features are identified within the 3D model based on positional comparisons between the geometry of the 3D model and the template model. In another example, after a scan to generate a 3D model, a human operator observes the 3D model and identifies anatomical structures of interest, in a similar manner as with generating the markers 302.

During a procedure, the workstation 12 processes the image obtained with the endoscope camera 204 to identify pixels of the image associated with particular identified anatomical structures. In some examples, different anatomical structures are recognized with different image processing techniques. In one technique, the workstation 12 identifies a dark area in an otherwise bright image (accounting for lighting- and/or camera-based vignetting) as an ostium. The workstation 12 determines which ostium is identified based on the position and direction of the distal end 208 of the endoscope probe 206. For example, based on the position within the 3D model, the workstation 12 may be able to identify that the distal end 208 of the endoscope probe 206 is within a particular area such as the nasal cavity and that the identified ostium is the maxillary sinus ostium based on the position of the distal end 208 of the endoscope probe 206 within the nasal cavity. In response, the workstation 12 draws an outline around the darkened area and provides a label identifying the outline as corresponding to the maxillary sinus ostium.

In another technique, the workstation 12 identifies an area of a particular color as being a particular type of anatomical structure. In FIG. 5B, a structure having a somewhat yellow color is identified as a nasal polyp based on its color and location. Specifically, the workstation 12 determines that the distal end 208 of the endoscope probe 206 is within the nasal cavity based on the position determined via interaction with the sensor 32 and thus determines that the yellow object in the image taken with the endoscope camera 204 is a nasal polyp.

Note that while certain overlay features are described herein, the present disclosure is not limited to those specific overlay features. Other overlay features that are technically feasible to draw may be displayed alternatively or additionally. The manner in which an overlay feature is displayed may be adjusted in location, form, and/or format based on image analysis of the image provided by the endoscope camera 204.

Figure 6:
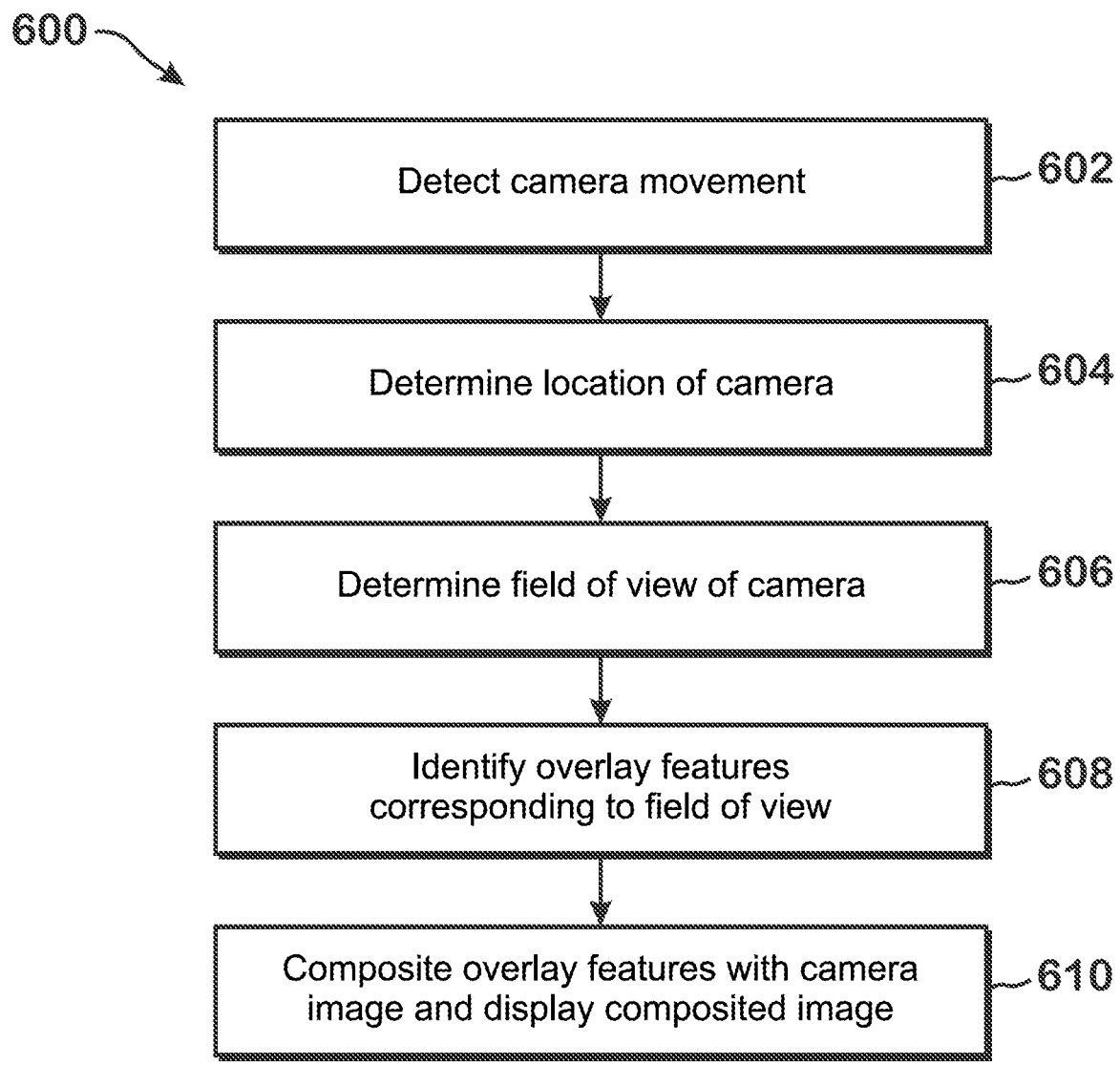
FIG. 6 is a flow diagram of a method for displaying an augmented reality image, according to an example.

FIG. 6 is a flow diagram of a method 600 for displaying an augmented reality image, according to an example. Although described with respect to the system described in conjunction with FIGS. 1-5B, those of skill in the art will understand that any system configured to perform the method with any technically feasible order of steps falls within the scope of the present disclosure. The method 600 illustrated may be performed for either or both of the camera 44 or the endoscope camera 204, or for any other camera included in the system 100. In the discussion of FIG. 6, the term "camera" without a reference number refers to any of these cameras.

As shown, the method 600 begins at step 602, where the workstation 12 detects the movement of a camera. This movement is detected via the location pad 30, which emits a signal that is received by one or more sensors 32 attached to the camera, as described above. A detection of movement corresponds to a detection that the location of the camera is different than the immediately previous location.

At step 604, the workstation 12 determines the location of the camera. Again, this location detection is based on signals received with the sensors 32 in response to signals transmitted by the location pad 30. Aspects of the signals are related to, and thus can be used to, determine location and orientation of the camera. For example, multiple emitters within the location pad 30 may emit different signals, each with different distinguishing characteristics (such as frequency). The sensors 32 detect the amplitude of the signals of different frequencies. The amplitude is associated with the distance from each of the emitters within the location pad 30. Each emitter has a known location in the location pad. Multiple distances are used to triangulate a position for a sensor 32. A sensor 32 may have individual microsensors that each receives a slightly different signal. The differences of the signals received with the microsensors may be used to determine orientation of the sensors 32. Via this analysis, the location and orientation of the sensor 32 with respect to the location pad 30 is determined. The location and orientation of the location pad 30 relative to the subject (e.g., a patient's head) is previously established based on a registration procedure, in which an operator such as a human operator moves a tool 10 having a sensor 32 around the subject and correlates one or more points on the subject to points in a 3D model of the subject, substantially as described above.

At step 606, the workstation 12 determines the field of view of the camera. The image generated by the camera is associated with a particular field of view, both in the real image (that is, the image actually generated by the camera) and in the 3D coordinate system corresponding to the 3D model and sensor 32 measurements. Any particular camera system has a known field of view, generally measured in degrees, which is determined based on characteristics of the lens and the sensor. An additional parameter associated with field of view is shape, some examples of which are rectangular and circular. Because the field of view is known based on physical features of the camera and sensor, determining the field of view of the camera involves looking up the field of view of the camera from stored data, calculating the field of view from other known parameters of the camera, or identifying the field of view through other known techniques—any technically feasible technique may be used.

At step 608, the workstation 12 identifies overlay features that correspond to the determined field of view. As described above, the overlay features include graphical elements associated with particular locations in the 3D space of the model stored in model data 48. One type of overlay feature is markers 302 that are associated with a particular point in the 3D space of the model. Another type of overlay feature include automatically generated indicators based on anatomy, such as the anatomical feature outlines 502 of FIGS. 5A-5B. This list of overlay features should not be taken to be limiting. Any type of feature or aspect related to a procedure and/or anatomy could be identified for compositing into the image to be viewed (e.g., the overview image 210 or the endoscope image 212).

At step 610, the workstation 12 composites the overlay features with the camera image and displays the composited image. The display on which the workstation 12 displays the positive image may depend on which camera the image came from and whether another camera of the system 100 is active and providing image data to the workstation 12 for display. In one example, if both the camera 44 and the endoscope camera 204 are active and providing images for compositing, then the workstation 12 displays the image from the camera 44 on the display 16, as overview image 210 and displays the image from the endoscope camera 204 on the endoscope display 205, as endoscope image 212. In another example, if both the camera 44 and the endoscope camera 204 are active and providing images for compositing, then the images are both displayed on the display 16, with time-based switching between the images, or with a selection of which image is displayed being controlled by a human operator. In yet another example, both images are displayed on a particular display, such as the display 16 or the endoscope display 205. In such a situation, the particular image being shown may be controlled by a human operator. Alternatively, one camera may have precedence over the other camera such that if one camera is switched on, then the display always displays the image from that camera and not from the other camera.

The overlay feature compositing comprises locating the overlay features identified at step 608 within the image associated with the camera and compositing those overlay features within the image received from the camera. Compositing the overlay features includes generating a graphical representation of the overlay feature and displaying that graphical representation together with the image from the camera (e.g., over the image from the camera or with pixels blended with pixels of the image from the camera). For the markers 302, a graphical representation may include an arrow 406 and text 408 generated as described with respect to FIGS. 4A-4C. Other overlay features may include the anatomical feature outlines generated as described with respect to FIG. 5A-5B. Some overlay features include visual indications of the tools 10. Specifically, the workstation 12 knows the position of the camera in the 3D space of the model and knows the position of the tools 10 in the 3D space of the model. If a tool is within the field of view of the camera, the workstation 12 can generate a graphical indicator of that tool to composite into the image generated by the camera.

The result after step 610 is an image from the camera, overlaid with one or more graphical features derived from data related to a 3D model and/or other stored data related to anatomy or a procedure being performed. The composited image may be displayed in the display 16 or the endoscope display 205.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements method described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for providing an augmented reality display of a subject, the method comprising:
    obtaining an image from a camera;
    identifying a location of the camera based on signals, wherein signals are received from sensors of a location pad in proximity of the subject's head wherein the location pad is not attached to the patient's head and receiving signals with sensors of the location pad, the signals generated by one or more field generators coupled to the camera;
    identifying a field of view of the camera based on the location of the camera;
    determining pixel value information of pixels corresponding to anatomical features in the field of view of the image;
    identifying one of the anatomical features of the subject based on the pixel value information and the location of the camera;
    generating one or more overlay features corresponding to the one anatomical feature in the field of view, the overlay features selected from a group comprising an anatomical feature outline of a sinus ostium and a text configured to label the sinus ostium;
    identifying the sinus ostium based on detection of a darkened portion of the image;
    in response to the identified sinus ostium, generating the outline of the identified ostium and generating the text on a selected location of the image, said selected location based on a variance of an average color value below a predetermined threshold for a plurality of pixels in an area of the image; and
    compositing the generated overlay features for the identified sinus ostium with the image from the camera to form a composited image;
    displaying the composited image on a display; and
    navigating one or more tools within the sinus ostium based upon the composited image.

2. The method of claim 1, wherein
    determining the pixel value information comprises determining at least one of brightness values of the pixels and color values of the pixels corresponding to the anatomical features in the field of view, and
    identifying the one anatomical feature of the subject comprises identifying the one anatomical feature based on at least one of: brightness values of pixels of the one anatomical feature relative to pixels of other anatomical feature in the field of view; and color values of pixels of the one anatomical feature in the field of view.

3. The method of claim 1, wherein detecting the location of a camera comprises:
    performing a pre-procedure registration to correlate a relative position and orientation of the location pad in comparison to a position and orientation of the subject.

4. The method of claim 1, wherein the one or more overlay features are associated with the one or more tools and generating the one or more overlay features comprises:
    generating a graphical representation of a tool.

5. The method of claim 4, wherein generating the graphical representation of the tool comprises:
    determining a position of the tool within the field of view of the camera; and
    rendering the graphical representation of the tool based on the position of the tool within the field of view of the camera.

6. The method of claim 1, wherein generating the overlay feature indicative of the anatomical feature comprises:
    determining a position of a marker within the field of view of the camera based on the relative position and orientation of the location pad and the position and orientation of the subject, and based on a relative location of the marker and a model of the subject; and
    rendering a graphical representation corresponding to the marker based on the position of the marker within the field of view of the camera.

7. The method of claim 6, wherein the graphical representation corresponding to the marker includes the text and an arrow as indicated by the marker.

8. The method of claim 6, wherein the graphical representation corresponding to the marker is adjusted in location, form, and/or format, based on image analysis of the image.

9. A system for providing an augmented reality display of a subject, the system comprising:
    a workstation; and
    a camera,
    wherein the workstation is configured to:
    obtain an image from the camera;
    identify a location of the camera based on signals, wherein signals are received from sensors of a location pad in proximity of the subject's head wherein the location pad is not attached to the patient's head and receiving signals with sensors of the location pad, the signals generated by one or more field generators coupled to the camera;
    identify a field of view of the camera based on the location of the camera;
    determine pixel value information of pixels corresponding to anatomical features in the field of view of the image;
    identify one of the anatomical features of the subject based on the pixel value information and the location of the camera;
    generate one or more overlay features corresponding to the one anatomical feature in the field of view, the overlay features selected from a group comprising an anatomical feature outline of a sinus ostium and a text configured to label the sinus ostium;
    identify the sinus ostium based on detection of a darkened portion of the image;
    in response to the identified sinus ostium, generating the outline of the identified ostium and generating the text on a selected location of the image, said selected location based on a variance of an average color value below a predetermined threshold for a plurality of pixels in an area of the image; and
    composite the generated overlay features for the identified sinus ostium with the image from the camera to form a composited image;
    display the composited image on a display; and navigate one or more tools within the sinus ostium based upon the composited image.

10. The system of claim 9, wherein
determining the pixel value information comprises determining at least one of: brightness values of the pixels corresponding to the anatomical features in the field of view; and color values of the pixels corresponding to the anatomical features in the field of view, and
identifying the one anatomical feature of the subject comprises identifying the one anatomical feature based on at least one of: brightness values of pixels of the one anatomical feature relative to pixels of other anatomical feature in the field of view; and color values of pixels of the one anatomical feature in the field of view.

11. The system of claim 9, further comprising the location pad, wherein the workstation is configured to detect the location of the camera by:
performing a pre-procedure registration to correlate a relative position and orientation of the location pad in comparison to a position and orientation of the subject.

12. The system of claim 9, wherein the one or more overlay features are associated with the one or more tools and the workstation is configured to generate the one or more overlay features by:
generating a graphical representation of a tool.

13. The system of claim 12, wherein the workstation is configured to generate the graphical representation of the tool by:
determining a position of the tool within the field of view of the camera; and
rendering the graphical representation of the tool based on the position of the tool within the field of view of the camera.

14. The system of claim 9, wherein the workstation is configured to generate the overlay feature indicative of the anatomical feature by:
determining a position of a marker within the field of view of the camera based on the relative position and orientation of the location pad and the position and orientation of the subject, and based on a relative location of the marker and a model of the subject; and
rendering a graphical representation corresponding to the marker based on the position of the marker within the field of view of the camera.

15. The system of claim 14, wherein the graphical representation corresponding to the marker includes the text and an arrow as indicated by the marker.

16. A system for providing an augmented reality display of a subject, the system comprising:
a workstation;
a display;
one or more tools;
a camera,
an endoscope; and
wherein the workstation is configured to:
obtain an image from the camera;
identify a location of the camera based on signals, wherein signals are received from sensors of a location pad in proximity of the subject's head wherein the location pad is not attached to the patient's head and receiving signals with sensors of the location pad, the signals generated by one or more field generators coupled to the camera;
identify a field of view of the camera based on the location of the camera;
determine pixel intensity information of pixels corresponding to anatomical features in the field of view of the image of the camera;
identify one of the anatomical features of the subject based on the pixel intensity information and the location of the camera;
generate one or more overlay features corresponding to the one anatomical feature in the field of view, the overlay features selected from a group comprising an anatomical feature outline of a sinus ostium and a text configured to label the sinus ostium;
identify the sinus ostium based on detection of a darkened portion of the image;
in response to the identified sinus ostium, generating the outline of the identified ostium and generating the text on a selected location of the image, said selected location based on a variance of an average color value below a predetermined threshold for a plurality of pixels in an area of the image; and
composite the generated overlay features for the identified sinus ostium with the image from the camera to form a composited image;
display the composited image on the display; and
navigate the one or more tools within the sinus ostium based upon the composited image.

17. The system of claim 16, wherein the camera is an endoscope camera.

* * * * *